US012599907B2

(12) United States Patent
Lansing et al.

(10) Patent No.: US 12,599,907 B2
(45) Date of Patent: Apr. 14, 2026

(54) INCUBATION CASSETTE AND MICROPLATE FOR REDUCING FLUID EVAPORATION OUT OF WELLS OF A MICROPLATE

(71) Applicant: TECAN TRADING AG, Mannedorf (CH)

(72) Inventors: Manfred Lansing, Salzburg (AT); Nicole Eggenhofer, Kuchl (AT); Tobias Sawetzki, Bischofswiesen (DE)

(73) Assignee: TECAN TRADING AG, Mannedorf (CH)

( * ) Notice: Subject to any disclaimer, the term of this patent is extended or adjusted under 35 U.S.C. 154(b) by 932 days.

(21) Appl. No.: 17/787,739

(22) PCT Filed: Dec. 30, 2019

(86) PCT No.: PCT/EP2019/087151
§ 371 (c)(1),
(2) Date: Jun. 21, 2022

(87) PCT Pub. No.: WO2021/136584
PCT Pub. Date: Jul. 8, 2021

(65) Prior Publication Data
US 2023/0083515 A1 Mar. 16, 2023

(51) Int. Cl.
*B01L 3/00* (2006.01)
*B01L 7/00* (2006.01)
(Continued)

(52) U.S. Cl.
CPC ............. *B01L 3/50851* (2013.01); *B01L 7/00* (2013.01); *B01L 9/523* (2013.01); *C12M 23/12* (2013.01);
(Continued)

(58) Field of Classification Search
None
See application file for complete search history.

(56) References Cited

U.S. PATENT DOCUMENTS 5,587,321 A * 12/1996 Smith .................... C12M 41/30
422/534
5,908,776 A * 6/1999 Burbaum .................. B01L 7/00
435/305.3
(Continued)

FOREIGN PATENT DOCUMENTS

DE 102016111075 A1 12/2017
EP 2943797 B1 10/2018
WO 2018081142 A1 5/2018

OTHER PUBLICATIONS

Mascarenhas et al., Design and development of components of a modular bioreactor, Dec. 5, 2017, Thesis: Massachusetts Institute of Technology, Department of Mechanical Engineering (Year: 2017).*
(Continued)

*Primary Examiner* — Holly Kipouros
(74) *Attorney, Agent, or Firm* — Notaro, Michalos & Zaccaria P.C.

(57) ABSTRACT

An incubation cassette for reducing liquid evaporation from wells of a microplate with a frame for receiving a microplate with wells, the frame having a central first opening surrounded by an inner wall, the dimensions are designed for inserting a microplate, and the frame having an outer wall that runs essentially parallel to the inner wall and which is attached to the inner wall connects so that a liquid reservoir surrounding the first central opening for receiving a liquid is formed by the two walls and the intermediate base is disclosed. The incubation cassette also includes a float provided in the liquid reservoir that can be brought into fluid contact with the liquid held in the liquid reservoir in such a way that the float is in relation to the liquid level of the liquid (Continued)

in the liquid reservoir absorbed liquid experiences buoy-
ancy.

35 Claims, 12 Drawing Sheets

(51) Int. Cl.
| | |
|---|---|
| *B01L 9/00* | (2006.01) |
| *C12M 1/00* | (2006.01) |
| *C12M 1/32* | (2006.01) |
| *C12M 1/34* | (2006.01) |
| *C12M 3/00* | (2006.01) |
| *G01F 23/68* | (2006.01) |

(52) U.S. Cl.
CPC ............ *C12M 23/38* (2013.01); *C12M 23/42*
(2013.01); *C12M 41/14* (2013.01); *C12M*
*41/34* (2013.01); *G01F 23/686* (2013.01);
*B01L 2200/142* (2013.01); *B01L 2300/0829*
(2013.01); *B01L 2300/185* (2013.01)

(56) References Cited

U.S. PATENT DOCUMENTS

| | | | |
|---|---|---|---|
| 2008/0003649 A1 | 1/2008 | Maltezos et al. | |
| 2016/0003859 A1* | 1/2016 | Wenczel | G01N 35/04 |
| | | | 422/561 |
| 2018/0187136 A1* | 7/2018 | Lichtenberg | B01L 3/5025 |

OTHER PUBLICATIONS

International Search Report for corresponding PCT application No.
PCT/EP2019/087151, mailed Oct. 5, 2020.

* cited by examiner

INCUBATION CASSETTE AND MICROPLATE FOR REDUCING FLUID EVAPORATION OUT OF WELLS OF A MICROPLATE

The invention relates to an incubation cassette for reducing liquid evaporation from the wells of a microplate, a microplate, a method for reducing liquid evaporation from the wells of a microplate and a microplate reader.

Microplate readers, with which the contents of one or more wells of a microplate can be examined or analyzed optically, have been known for a long time. In connection with the present invention, a microplate is any multiwell plate that has a large number of wells or containers that are arranged, for example, in an array. Particularly preferred microplates have at least approximately the mass and footprint of a microplate according to the SBS standard as published by the American National Standards Institute (ANSI). For example, such standard microplates are known whose wells are equipped with a round bottom, flat bottom or V-bottom. All of these standard microplates with the most varied of well shapes have in common that the axial spacing of the wells arranged in an array is also standardized (cf. ANSI_SBS 1-2-3-4-2004 standard for microplate dimensions from the year 2006). This axial distance is e.g. 18 mm for 24-well (4×6) plates, 9 mm for 96-well (8×12) plates, and 9 mm for 384-well (16×24) plates 4.5 mm, and for 1536-well (32×48) plates 2.25 mm. The height of a standard microplate can vary greatly depending on the type and is typically between 10.4 mm (e.g. 1536 V-bottom deep well plate) and 44 mm (e.g. 96 well Masterblock® from Greiner).

Known microplate readers are equipped with corresponding light sources and/or detectors for assaying samples respectively samples provided with test solution, in the wells of microplates based on the absorption, fluorescence and/or luminescence thereof. Usually, the samples are located in a test solution which is exposed to environmental influences. Particularly in the case of long-term experiment series using cell cultures in the wells, which are typically carried out in stand-alone microplate readers over hours or even days and possibly also at elevated temperatures compared to room temperature, evaporation problems may arise for the samples or the test solution containing the samples. The evaporation of the test solution leads to a thickening and thus to a change in the concentration of buffer substances and molecules to be assayed (analytes). This changes for example the growth conditions for cell-based experiments and/or the reaction of cells to experiment-induced influences. It has also been observed that the test solution of wells arranged in the corners of a standard microplate suffers from such evaporation problems more than that of wells arranged in the middle of a microplate. This in turn means that the thickening does not occur in a manner distributed homogeneously across all wells of a microplate, but instead leads to differences, and thus to non-comparable results, within the same experiment series.

Devices for preventing or reducing such evaporation problems are known from the prior art. For instance, the patent EP 2943797 B1 discloses an incubation cassette for reducing liquid evaporation from wells of a microplate, wherein the incubation cassette comprises a frame for receiving a microplate. The incubation cassette also provides a reservoir which can be filled with liquid, said reservoir being in the form of a liquid channel which surrounds the inserted microplate. As a result, the atmosphere in the immediate vicinity of the wells of the microplate is enriched accordingly, so that any thickening of the sample liquid caused by evaporation can be delayed.

In the prior art, however, the liquid in the liquid channel may evaporate completely, as a result of which the atmosphere in the immediate vicinity of the microplate wells is no longer enriched. The liquid level or amount of liquid in the liquid channel must therefore be checked frequently, and the liquid must be topped up manually in order to maintain the functionality. The checking and manual topping-up of the liquid channel take a lot of time and effort. Another disadvantage is that the liquid channel cannot be topped up with liquid during some measurements, particularly in the case of long-term measurements, without introducing disturbances into the experiment.

The object of the present invention is therefore to propose an incubation cassette for reducing liquid evaporation from the wells of a microplate, a microplate, a method for reducing liquid evaporation from wells of a microplate, a microplate reader, in which the disadvantages known from the prior art are eliminated.

This object is achieved by an incubation cassette for reducing liquid evaporation from the wells of a microplate according to claim 1. Furthermore, the object is achieved by a microplate, a method for reducing liquid evaporation from wells of a microplate, and a microplate reader according to further claims.

The incubation cassette according to the invention for reducing liquid evaporation from wells of a microplate comprises a frame for receiving a microplate with wells. The frame comprises a central first opening surrounded by an inner wall, the dimensions of which are designed for inserting a microplate, and an outer wall running essentially parallel to the inner wall, which connects to the inner wall via an intermediate floor, so that by the two walls and the intermediate floor a liquid reservoir surrounding the first central opening for receiving a liquid is formed. The incubation cassette further includes a float provided in the liquid reservoir, which can be brought into fluid contact with the liquid held in the liquid reservoir, such that the float experiences buoyancy in relation to the liquid level of the liquid held in the liquid reservoir.

The microplate according to the invention comprises a plurality of wells, the microplate being provided with at least one liquid reservoir. The microplate further includes a float provided in the liquid reservoir, which can be brought into fluid contact with the liquid held in the liquid reservoir such that the float experiences buoyancy in relation to the liquid level of the liquid held in the liquid reservoir.

The method according to the invention for reducing liquid evaporation from wells of a microplate comprises:

a) providing a microplate, b) adding a sample to at least one of the wells of the microplate, c) moving the microplate or an incubation cassette equipped with the microplate into a microplate reader, d) injecting a liquid into a liquid reservoir provided in the microplate and/or the incubation cassette, e) performing measurements on the samples in the respective wells, f) measuring a liquid level in the liquid reservoir of the microplate and/or the incubation cassette by measuring the buoyancy of a float provided in the liquid reservoir of the microplate and/or the incubation cassette, g) re-injecting the liquid into the liquid reservoir of the microplate and/or the incubation cassette if the liquid level falls below a predetermined threshold value, h) repeating steps e) to g) until a predetermined number of measurement cycles is reached, i) ejecting the microplate or the incubation cassette fitted with the microplate from the microplate reader.

Further preferred and inventive subject matter result from the further claims, respectively.

Advantages of the invention comprise:

The liquid level in the liquid reservoir of the microplate and/or the incubation cassette can be monitored automatically, independently of the duration of a respective measurement of samples in the wells of the microplate.

The liquid reservoir of the microplate and/or the incubation cassette can be filled or refilled with liquid manually or automatically by an injector as soon as it is detected that the liquid level in the liquid reservoir falls below a predefined liquid level. As a result, the liquid reservoir remains reliably filled with liquid.

The liquid can be re-injected into the liquid reservoir of the microplate and/or the incubation cassette using an injector that is already included in the microplate reader. Thus, the samples or the samples provided with test solution are advantageously exposed to reduced fluctuations in temperature and/or atmosphere.

At least one device for optical measurement can be used for automated monitoring of the liquid level, in particular a device for measuring fluorescence emitted by the float, in particular a fluorescence module.

The float can be part of a float device that can be provided in the liquid reservoir of the microplate and/or incubation cassette. The float experiences buoyancy in relation to the liquid level of the liquid in the liquid reservoir. The float can have a lower density than the liquid it absorbs.

The float can be spherical or cylindrical. In a further example, the float can be triangular, square, star-shaped or irregular, with the guide section or the inner surface of the guide section being designed to correspond to the triangular, square, star-shaped or irregular shape of the float. The float can float freely in the guide section at the respective height of the liquid level of the liquid in the liquid reservoir. The float and the guide section are designed in relation to one another in such a way that the float can float upwards in the guide section without tilting.

In a fluorescence top-reading mode, the optics of the optical measuring device can be focused on the uppermost position of the float, which it assumes when the liquid reservoir is completely filled. As the liquid level decreases, the float moves out of focus, causing the measured fluorescence (emitted by the float) of the float to decrease. The measured fluorescence correlates with the liquid level in the liquid reservoir.

In a fluorescence bottom-reading mode, the optics of the optical measuring device can be focused on the lowest position of the float, which the float assumes when the liquid reservoir is completely empty. As the liquid level increases, the float moves out of focus, causing the measured fluorescence (emitted by the float) of the float to decrease. The measured fluorescence correlates with the liquid level in the liquid reservoir. In this mode, the fluorescence emitted by the float is measured optically through at least a transparent portion of the incubation cassette and/or microplate.

Based on the measured fluorescence, conclusions can be drawn about the liquid level in the liquid reservoir.

The device for measuring the fluorescence emitted by the float (hereinafter also referred to as fluorescence measurement of the float) can already be included in the microplate reader, e.g. a device for optically analyzing samples in the wells of the microplate. A fluorescence module is preferably used. This saves costs and space, since a device that is already included in the microplate reader can be used.

The float can be irradiated from above the microplate and/or the incubation cassette and its emitted fluorescence can also be detected from above the microplate and/or the incubation cassette.

The float can be irradiated from below the microplate and/or the incubation cassette and its emitted fluorescence can also be detected from below the microplate and/or the incubation cassette. In this case, the optical axis runs through a transparent section of the incubation cassette and/or a transparent section of the microplate, through which the microplate and/or the incubation cassette are optically accessible from below. The emitted light and the emission by the float each pass through the transparent section.

The incubation cassette is dimensioned and designed in such a way that it can be easily (manually or robotically) inserted into the transport support of a microplate reader and just as easily (manually or robotically) removed from this transport support.

A lid can be placed on the incubation cassette or microplate to isolate the enriched atmosphere from the environment. This lid can be lifted off and put on again inside the microplate reader, so that the microplate wells are freely accessible for the time required for all actions.

The gas exchange between the microplate wells and the environment, which is necessary for cell cultures or for cell-based experiments, can be supported by the operator by sporadically lifting the lid of the incubation cassette, by a robot or by a corresponding device in the microplate reader itself.

Any microplates can be placed in the incubation frame or in the incubation cassette, whereby standard microplates according to ANSI_SBS 1-2-3-4-2004 standard are preferred. This makes the use of special microplates superfluous for carrying out experiments with cell cultures or cell-based experiments.

Thanks to the use of an incubation cassette, long-term experiments can be carried out in a microplate reader even at elevated temperatures (e.g. at 37° C.).

The invention will be shown by way of example with the aid of schematic figures in the drawing. The figures are intended to document selected embodiments of the subject matter of the invention, but do not limit the scope of the present invention. In the figures:

FIG. 1 shows a view of an incubation cassette, with the lid removed, on a transport support of a microplate reader FIG. 2 shows a perspective view of an incubation cassette with an inserted microplate with a lid partially lifted off the incubation cassette;

FIG. 3A-C show detailed views of floating devices provided in a liquid reservoir with different liquid levels in each case;

FIG. 4 shows a vertical partial section through an incubation cassette and a floating device provided in a liquid reservoir of the incubation cassette;

FIG. 5A,B show detailed views of a microplate with a floating device that is placed differently in each case;

Figure 8A:
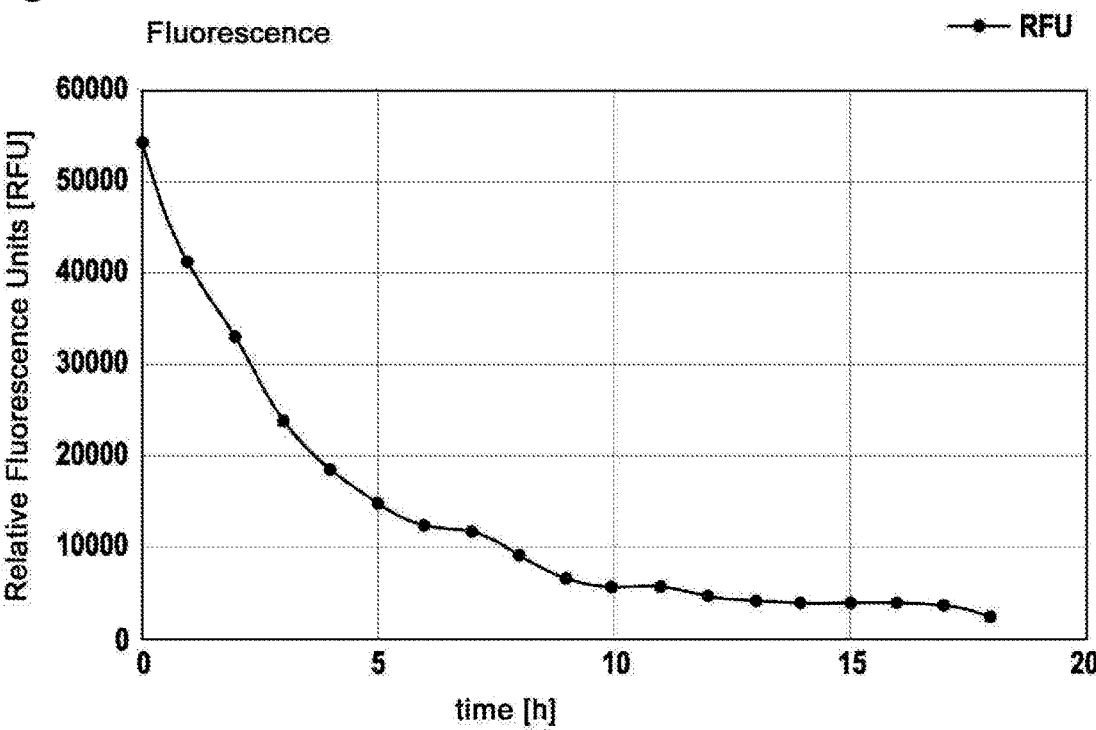
Figure 9A:
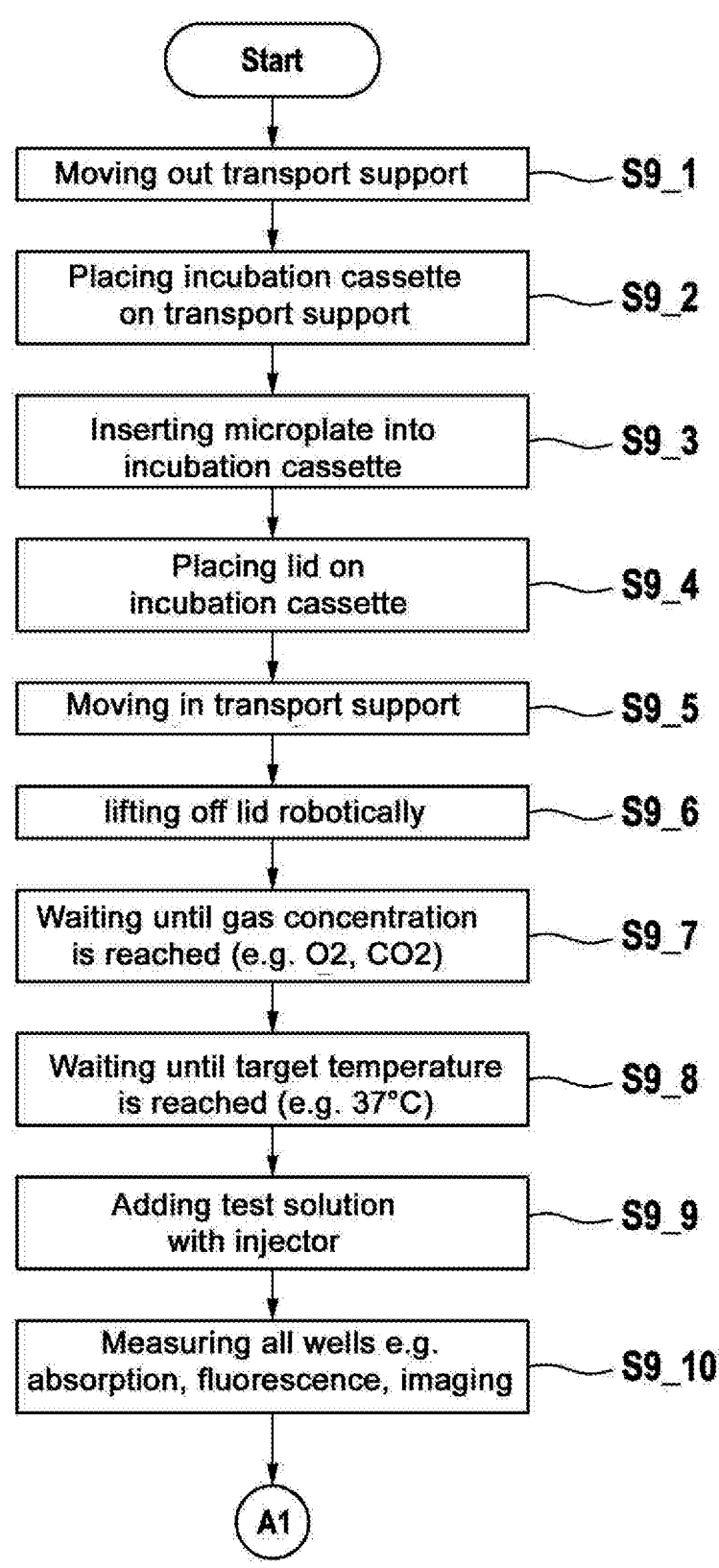
Figure 9B:
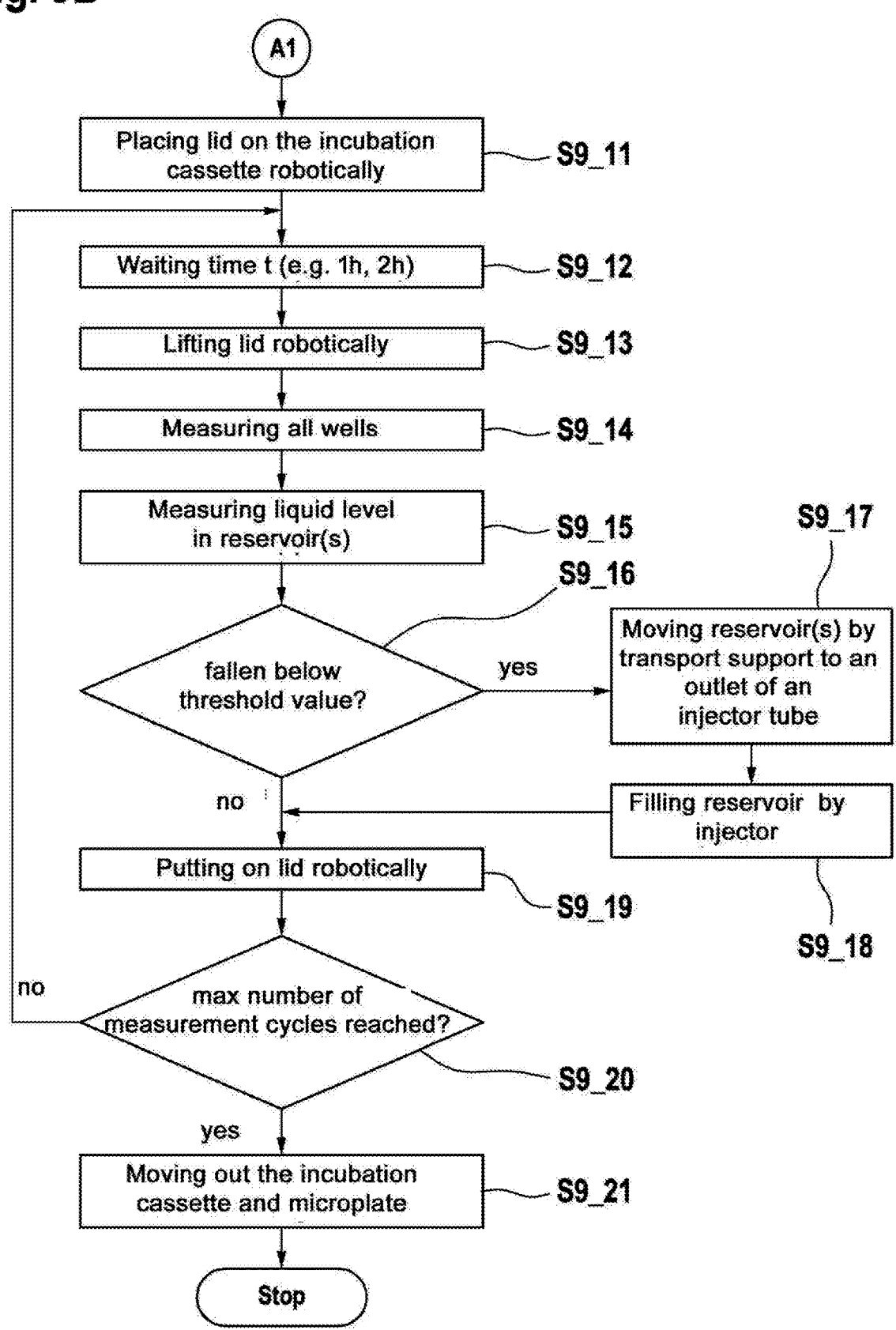
Figure 10A:
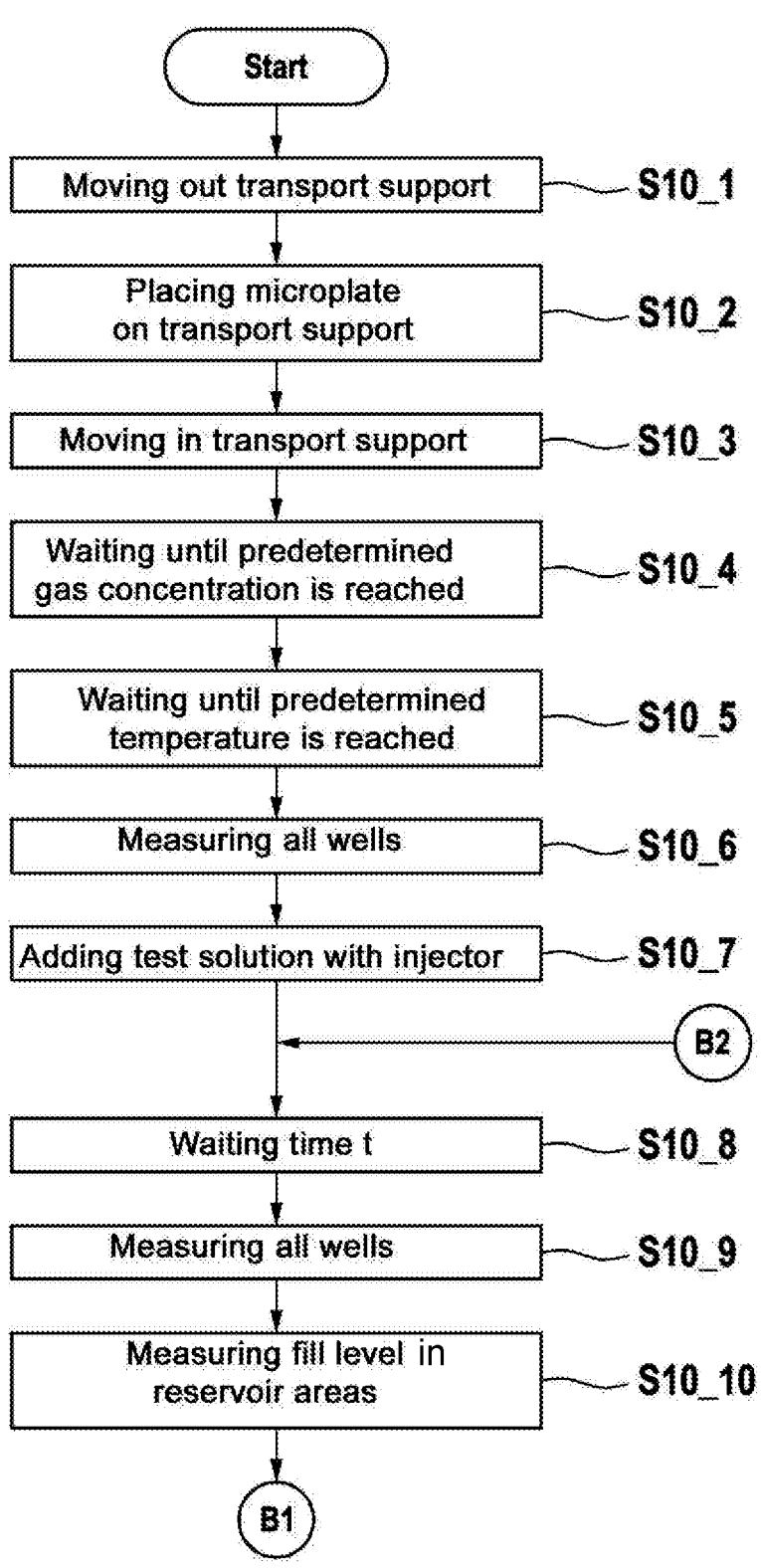
Figure 10B:
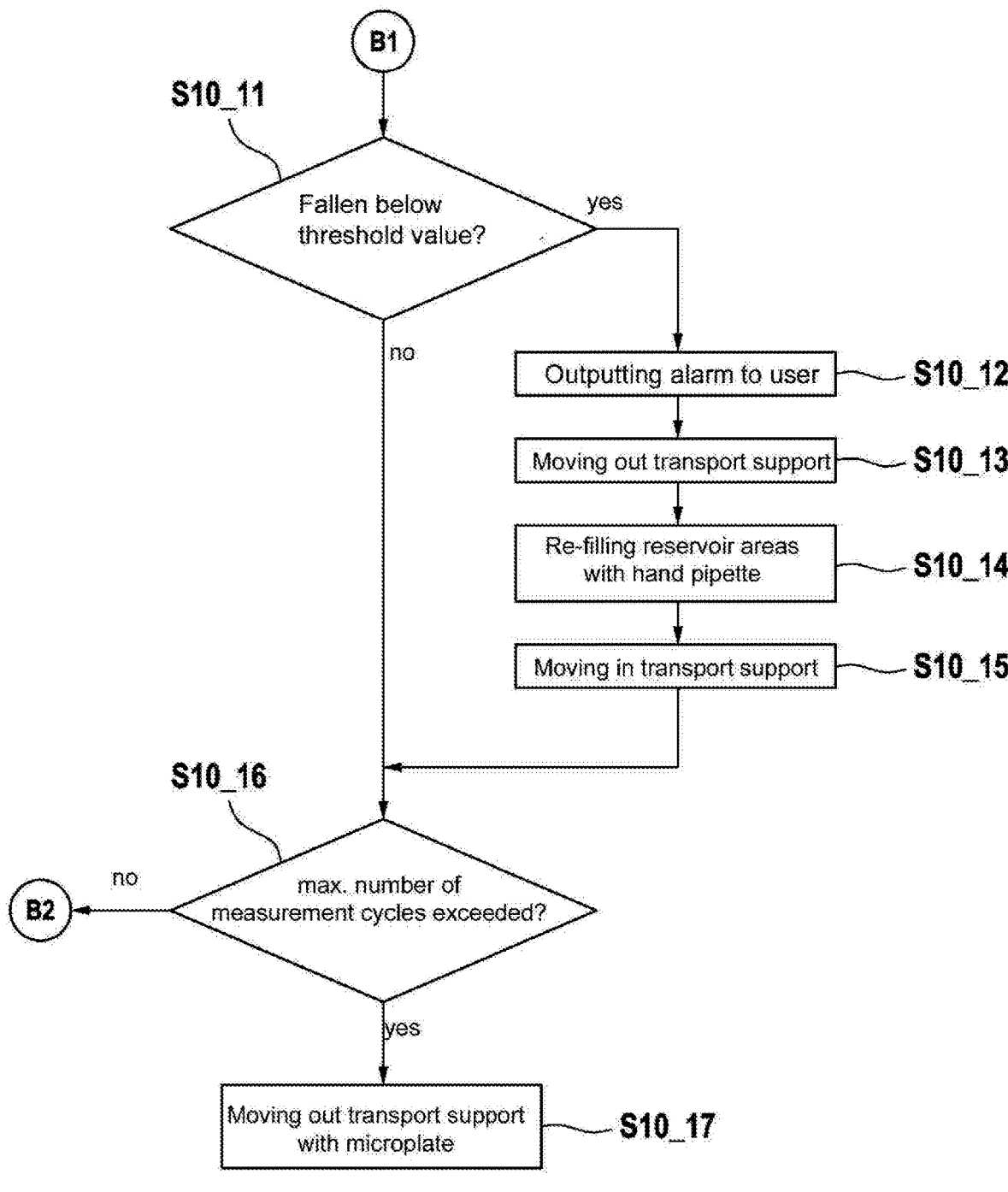

FIG. 8A,B show curves of a fluorescence measurement of the float and a liquid level derived therefrom, each plotted as a function of time;

FIG. 9A,B show a flowchart of a method for reducing liquid evaporation from wells of a microplate placed in an incubation cassette; and FIG. 10A,B show a flow chart of a method for reducing liquid evaporation from wells of a microplate.

Figure 1:
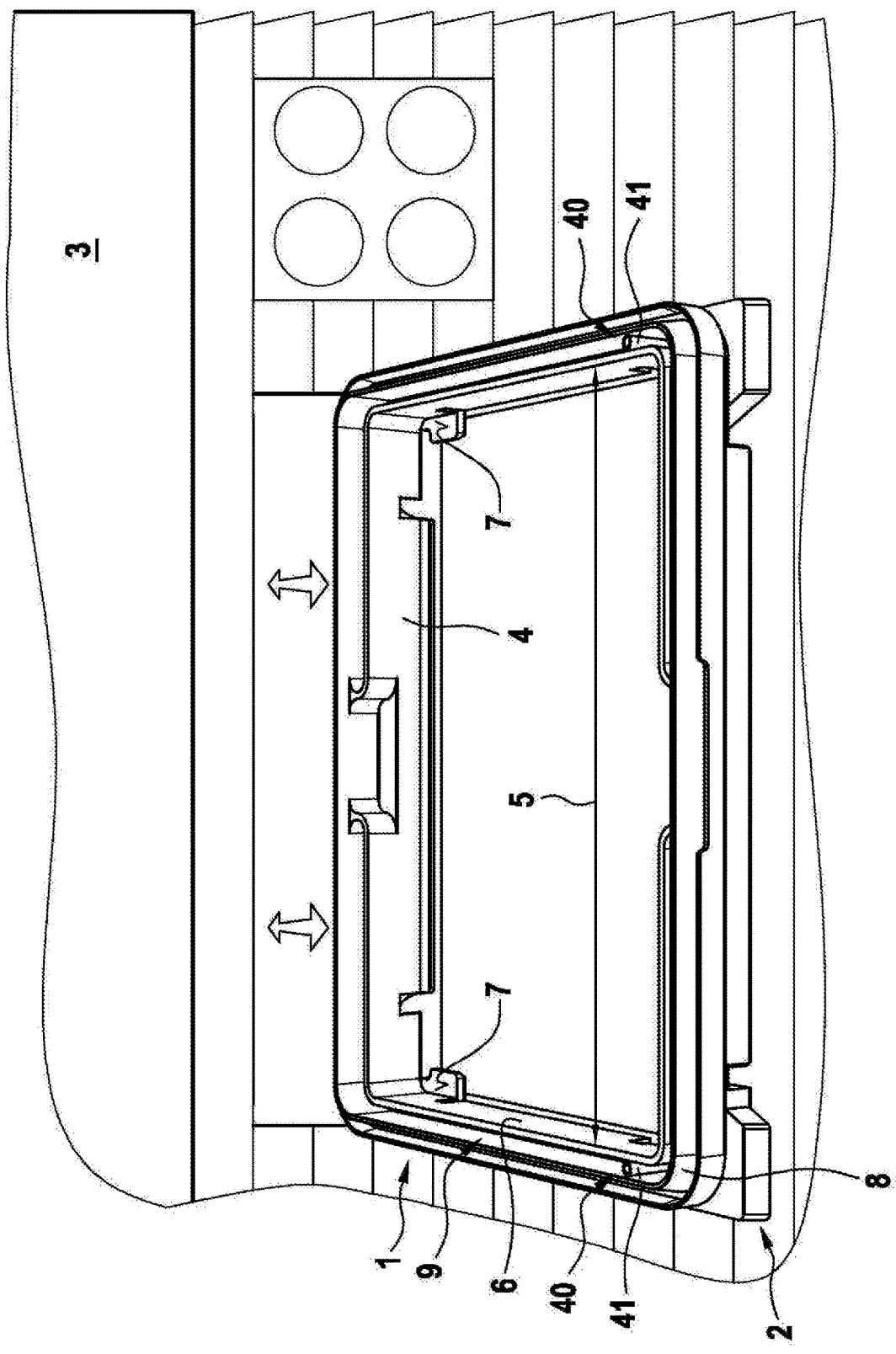

FIG. 1 shows an embodiment of an incubation cassette 1 according to the invention, which is placed on a transport support 2 of a microplate reader 3 for transporting the incubation cassette 1. A microplate, e.g. a standard microplate, can in turn be inserted into the incubation cassette 1 (not shown).

The incubation cassette 1 comprises a frame 4 onto which a lid can be placed (not shown). The frame 4 comprises a central first opening 5, the dimensions of which are designed for the complete insertion of the microplate. The central first opening 5 is surrounded by a preferably essentially vertical inner wall 6, with several essentially horizontal supporting surfaces 7 preferably being arranged at least in sections on the lower end thereof. These supporting surfaces 7 are used to carry the inserted microplate (not shown). The frame 4 of the incubation cassette 1 also includes an outer wall 8, which preferably runs essentially parallel to the inner wall 6 and is connected to the inner wall 6 via an intermediate floor, so that a channel for receiving a liquid, also called liquid reservoir 9, surrounding the central first opening 5 is formed by the two walls 6, 8 and the intermediate floor.

The incubation cassette 1 also includes a floating device 40 which is provided in the liquid reservoir 9. The floating device 40 comprises a guide section 41 and a float (not shown), which is supported by the guide section 41 so that it can be guided vertically. The guide section 41 can herein be a hollow cylinder in which the float is inserted. The float can be cylindrical or spherical, in which case the diameter of the float can be slightly smaller than the inside diameter of the guide section, so that the float can float upwards without tilting. The density of the float is lower than the density of the liquid contained in the liquid reservoir 9, so that the float can experience buoyancy. The float can be brought into fluid contact with the fluid contained in the fluid reservoir 9. The float thus experiences buoyancy in relation to the liquid level of the liquid contained in the liquid reservoir 9. This vertical displacement of the float (buoyancy) can in turn be optically detected in order to be able to determine the liquid level in the liquid reservoir 9, as described in detail below.

The guide section 41 can be formed in one piece with sections of the liquid reservoir 9. Alternatively, the guide section 41 can be removably connectable to sections of the liquid reservoir 9, e.g. by means of a plug-in connection. The guide section 41 is exposed to the atmosphere for pressure equalization via the opening at its upper end. The liquid can penetrate into the interior of the guide section 41 via an opening or a recess at the lower end of the guide section 41. Thus, the float experiences unhindered buoyancy or floats.

Figure 2:
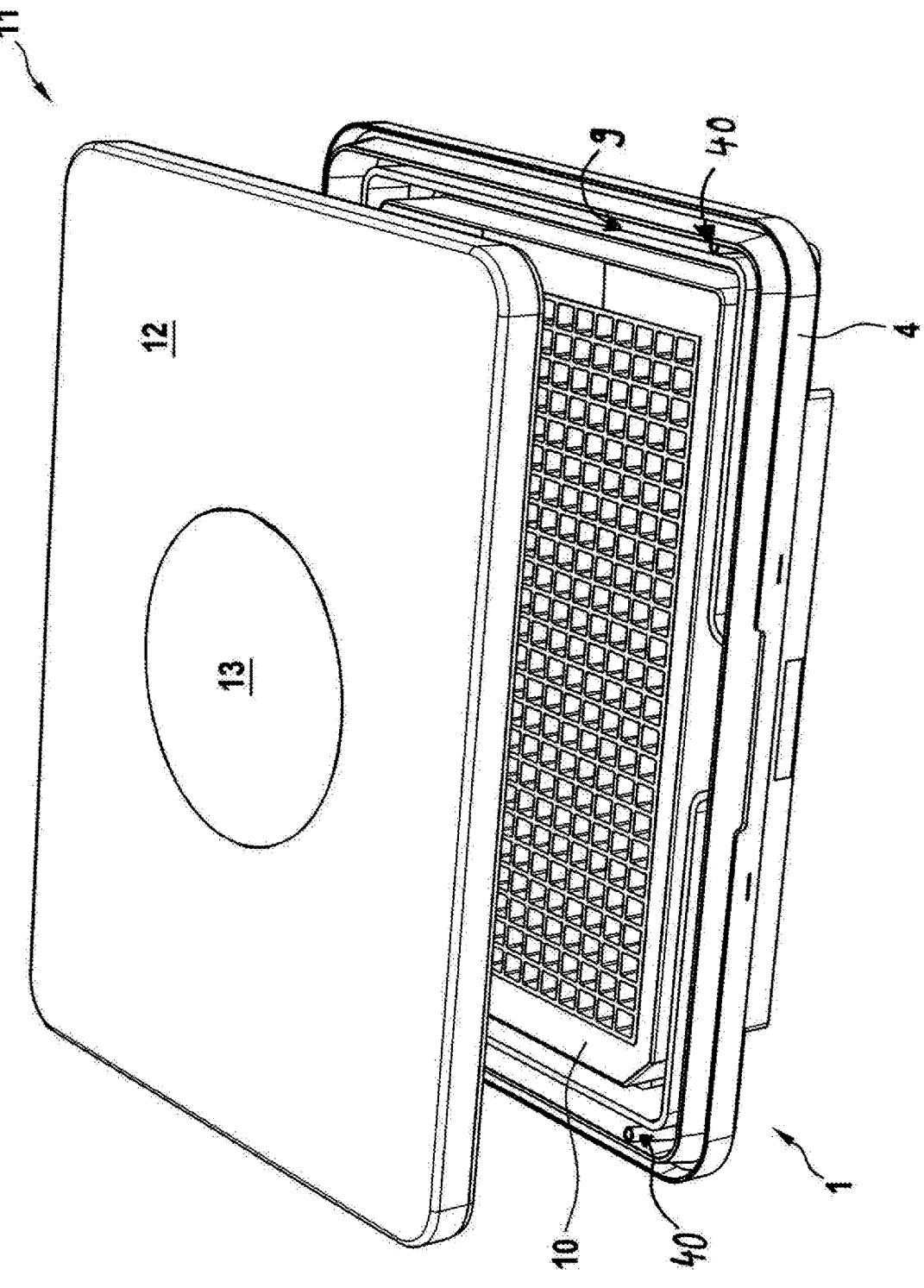

FIG. 2 shows a perspective view of a frame 4 of an incubation cassette 1 with an inserted microplate 10. In the example shown, the liquid reservoir 9 of the incubation cassette 1 is provided with floating devices 40 for determining the liquid level (in the figure, two floating devices 40 are recognizable, but the number is not limited to this). A lid 11 that has been partially lifted off the incubation cassette 1 is also shown. The lid 11 is used to cover the frame 4 with the inserted microplate 10. The lid 11 can be placed or removed inside or outside a microplate reader (not shown) manually or with a robot. The lid 11 shown comprises a plate 12 with a magnetizable surface 13 which can cover only part of the plate 12. Alternatively, several such small magnetizable surfaces or a single large magnetizable surface could be provided which at least approximately covers the entire plate 12. The magnetizable surface 13 can be selected from a group consisting of a self-adhesive metal foil, an over-moulded metal plate and a bonded metal plate, and wherein the metal can include: iron, nickel and their alloys. A microplate reader (not shown) can include a magnet device integrated in its housing for lifting and replacing the lid 11 of the incubation cassette 1 placed on a transport support. In an alternative example, the lid 11 can be lifted off and put on by means of a gripping cup or sucker (not shown). The lid 11 is preferably made of a chemically inert plastic and is produced, for example, by means of injection moulding.

Figure 3A:
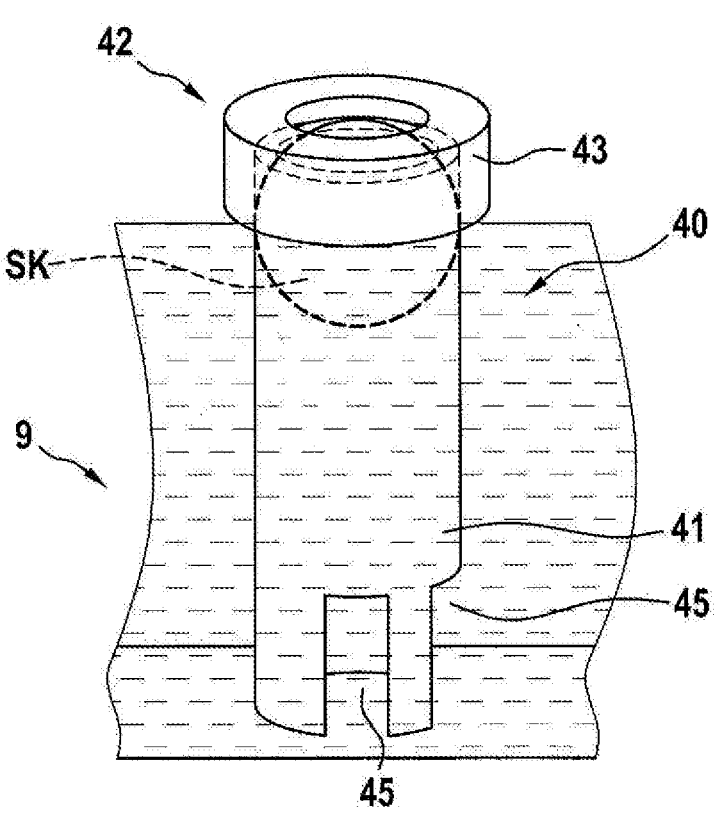
Figure 3B:
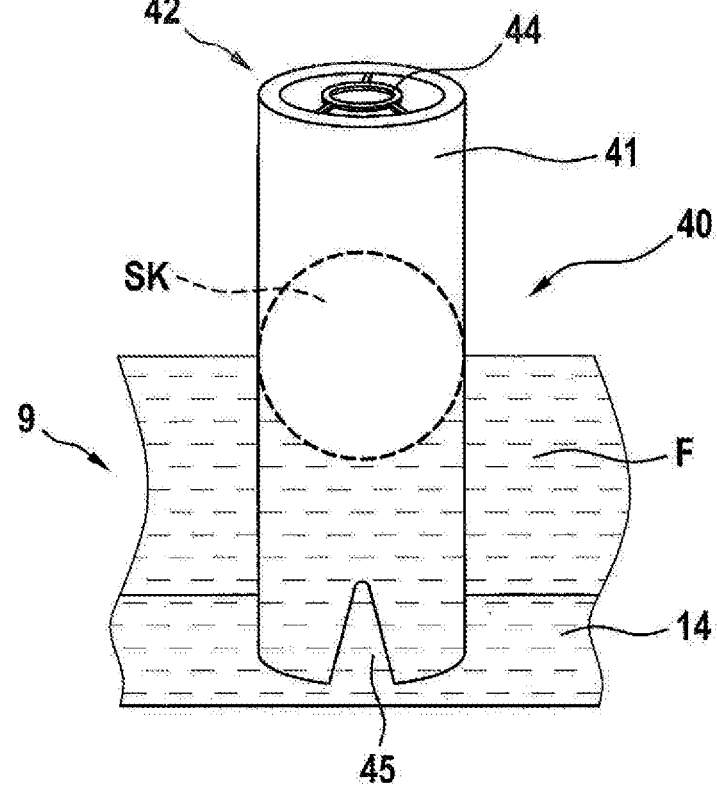
Figure 3C:
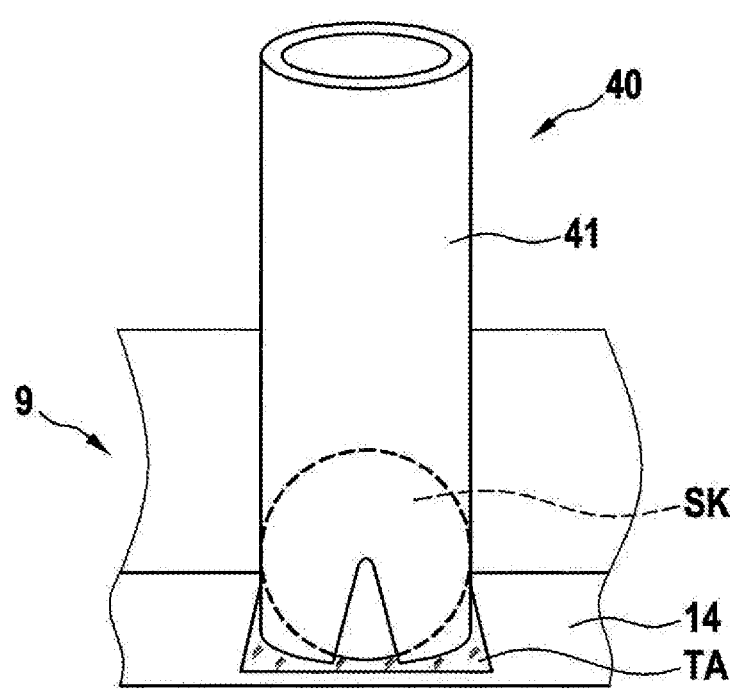

FIG. 3A-C show detailed views of floating devices 40 provided in a liquid reservoir 9 with different liquid levels in each case. The guide section 41 of the floating device 40 is cylindrical and accommodates a float SK in the form of a floating ball, for example. The float SK can also be cylindrical. The diameter of the float SK is slightly smaller than the inside diameter of the guide section 41. In a further example, the float can be triangular, square or star-shaped, with the guide section or the inner surface of the guide section corresponding to the triangular, square or star-shaped configuration of the float is formed. The float can also have an irregular shape, with the guide section or the inner surface of the guide section being designed to correspond to the irregular shape.

The lower section of the guide section 41, or that section of the guide section 41 which is exposed to the liquid, is provided with a number of rectangular recesses 45 through which the liquid F flows unhindered into the interior of the guide section 41 and out can. The upper end of the guide section 41 is open or exposed to the atmosphere in order to achieve pressure equalization. Thus, the floating ball SK can experience buoyancy or float unhindered in the guide section 41 through the liquid F. At the upper end of the guide section 41 there is a stop 42 against which the float SK can strike from the inside. This prevents the float SK from falling out of the guide section 41. In other words, the float SK is held back by the stop 42 inside the guide section 41. The stop 42 also allows the float SK to always and reliably assume an unchangeable position, also referred to as the reference position, when the liquid reservoir 9 is completely filled, through which a reliable focusing of the float SK can be made possible from above (fluorescence top-reading mode), as detailed below.

In the example shown in FIG. 3A, the stop 42 is designed as a cap 43 which is provided with a hole in its center, via which the pressure equalization between the interior of the guide section 41 and the atmosphere is ensured. The diameter of the hole is smaller than the diameter of the float SK so that it is reliably retained inside the guide section 41. In the example shown, the liquid reservoir 9 is completely filled with liquid F, so that the float SK floats at its uppermost position and hits the cap 43 from below.

In the embodiment shown in FIG. 3B, the recess 45 is triangular. The stop 42 is designed as a grid 44 against which the float SK can strike and pressure equalization can also be achieved. The liquid reservoir 9 is partially filled with liquid F. The float SK floats to the level of the liquid level. FIG. 3C shows the floating device 40 in a state in which the liquid reservoir 9 does not contain any liquid and the float SK does not experience any buoyancy.

In the example shown, the intermediate floor 14 of the liquid reservoir 9 is provided with a transparent section TA. The transparent section TA contains an optically transparent material, which can be optically transparent for light of for example a measuring device for measuring the fluorescence of the float SK. A fluorescence measuring device or a fluorescence module can be used to determine the height or buoyancy of the float SK from below the incubation cassette through the transparent section TA (fluorescence bottom reading mode), as described in detail below.

Figure 4:
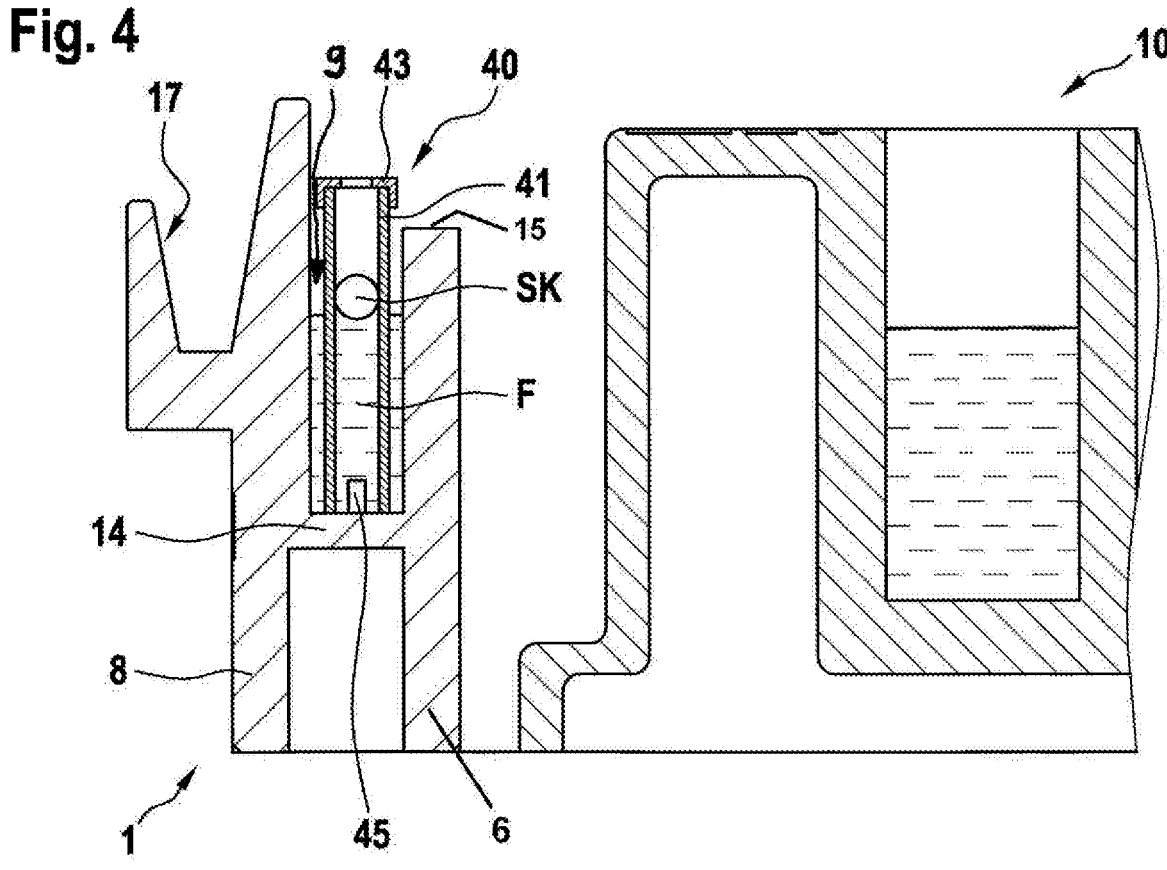

FIG. 4 schematically shows a vertical partial section through an incubation cassette 1, a microplate 10 inserted therein, and a floating device 40 provided in the liquid reservoir 9 of the incubation cassette 1. The incubation cassette 1 is preferably made of a chemically inert plastic and is produced, for example, by means of injection molding. The liquid reservoir 9 is defined by the outer wall 8, the intermediate floor 14 and the inner wall 6 and is filled with liquid F in the example shown.

In the incubation cassette 1 shown here, the inner wall 6 can include sunken areas 15 so that when the lid (not shown) is put on, each sunken area 15 connects the microplate 10 to the liquid reservoir 9 surrounding it. It can be provided that the inner wall 6 of the incubation cassette 1 is consistently less high than the outer wall 8, so that when the lid is put on, a circumferential gap connects the microplate 10 with the liquid reservoir 9 surrounding it. A continuous gas atmosphere is thus created above the liquid reservoir 9 and above the wells of the microplate 10. The incubation cassette 1 can comprise an integrally formed, circumferential recess 17 into which a downwardly protruding, circumferential edge of a lid (both not shown) can engage. In this way, a lid can be placed and removed safely and centered on the incubation cassette 1 without it being displaced or slipping when the incubation cassette 1 is shifted sideways, for example.

The floating device 40 shown in FIG. 4 is designed in the same way as the embodiment shown in FIG. 3A. The liquid F flows through the recess 45 at the lower end into the guide section 41 and out of it. The hole in the cap 43 placed on the upper end of the guide section 41 ensures pressure equalization between the interior of the guide section 41 and the atmosphere. The float SK thus reliably floats up to the liquid level of the liquid F in the liquid reservoir 9. The height or buoyancy of the float SK can be determined by a measuring device provided in a microplate reader (not shown) above the incubation cassette 1, e.g. a device for measuring fluorescence, in particular a fluorescence module (not shown), as described in detail below.

Although not shown, the intermediate floor 14 can be provided with a transparent section (see also FIG. 3C), through which the emitted fluorescence of the float SK can be measured or determined from below the incubation cassette 1. In this case, the incubation cassette 1 is designed in such a way that the irradiated excitation light and the fluorescence emitted by the float SK can run unhindered through the transparent section from below. In other words, there should be no portions that could block downwards an optical axis passing through each transparent portion.

Figure 5A:
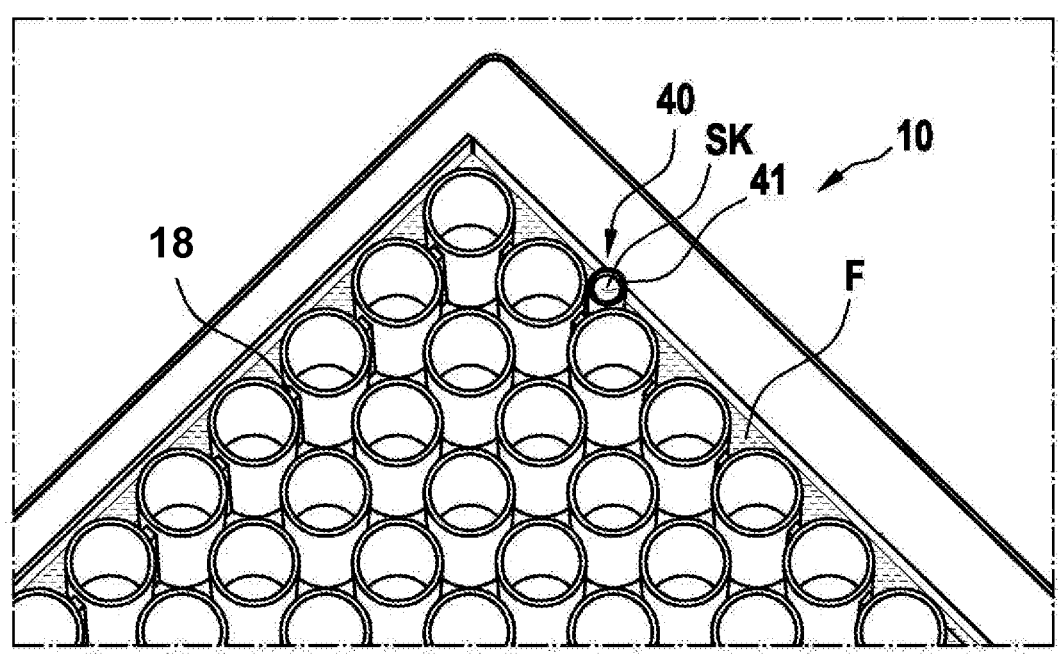

FIGS. 5A, B show detailed views of a microplate 10 with a floating device 40 placed differently in each case. The microplate 10 contains a plurality of wells which protrude from the bottom of the microplate 10 and are open at the top.

Figure 5B:
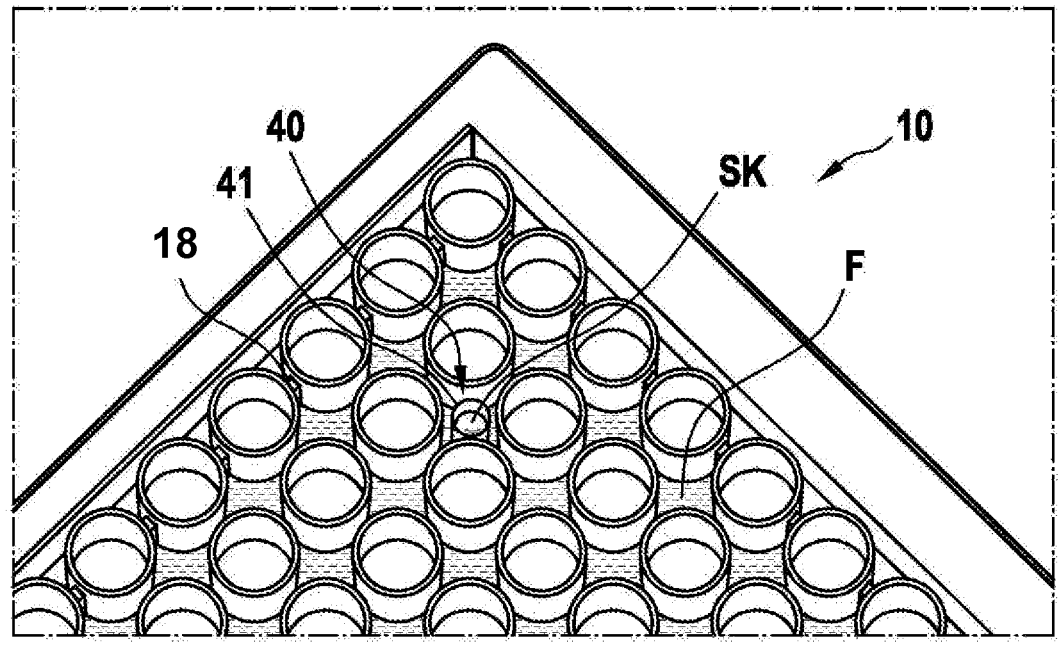

The microplate 10 is in turn delimited to the outside by a wall. The intermediate space thus provided forms a reservoir, also referred to as a liquid reservoir, for receiving liquid F. In the microplate 10 shown in the figures, the outer wells running parallel to the wall are connected by ridges 18. These ridges 18 divide the liquid reservoir into two partial reservoirs. As can be seen in the figures, a first partial reservoir is located in the section of the microplate 10 between the ridges 18 (and outer wells) and the wall and is shown filled with liquid F in FIG. 5A. A further partial reservoir is formed by the remaining (inner) portion of the microplate 10 and is shown filled with liquid F in FIG. 5B. Although not shown, both partial reservoirs can also be filled with liquid F.

The microplate 10 may be formed entirely, partially, or not at all from a transparent material. Black microplates are primarily used for top-reading fluorescence measurements, and white microplates for luminescence measurements. The microplate 10 shown in FIG. 5A comprises the floating device 40 in the partial reservoir provided at the outer edge. The outer diameter of the guide section 41 can be dimensioned in such a way that it can be inserted between the outward wall and the outer walls of two wells with a friction fit. The microplate 10 shown in FIG. 5B includes the floating device 40 in the sub-reservoir provided in the inner portion of the microplate 10. The partial reservoirs each provided with the floating device 40 are filled with liquid F, for example. The outer diameter of the guide section 41 can be dimensioned in such a way that it can be inserted between the outer walls of four wells with a friction fit. The float SK floats within the guide section 41 at the height of the liquid level. The liquid level can be determined by detecting the height or the buoyancy of the float SK. The height or the buoyancy of the float SK can be determined, for example, by measuring the fluorescence of the float SK using the fluorescence module (not shown). This fluorescence module can measure the fluorescence emitted by the float SK from above the microplate 10 and/or from below the microplate 10, through the transparent material thereof. However, measurements from below require transparent parts in the area of the guide section 41 or the float SK. Details on this are described in connection with the description of FIG. 6.

Figure 6:
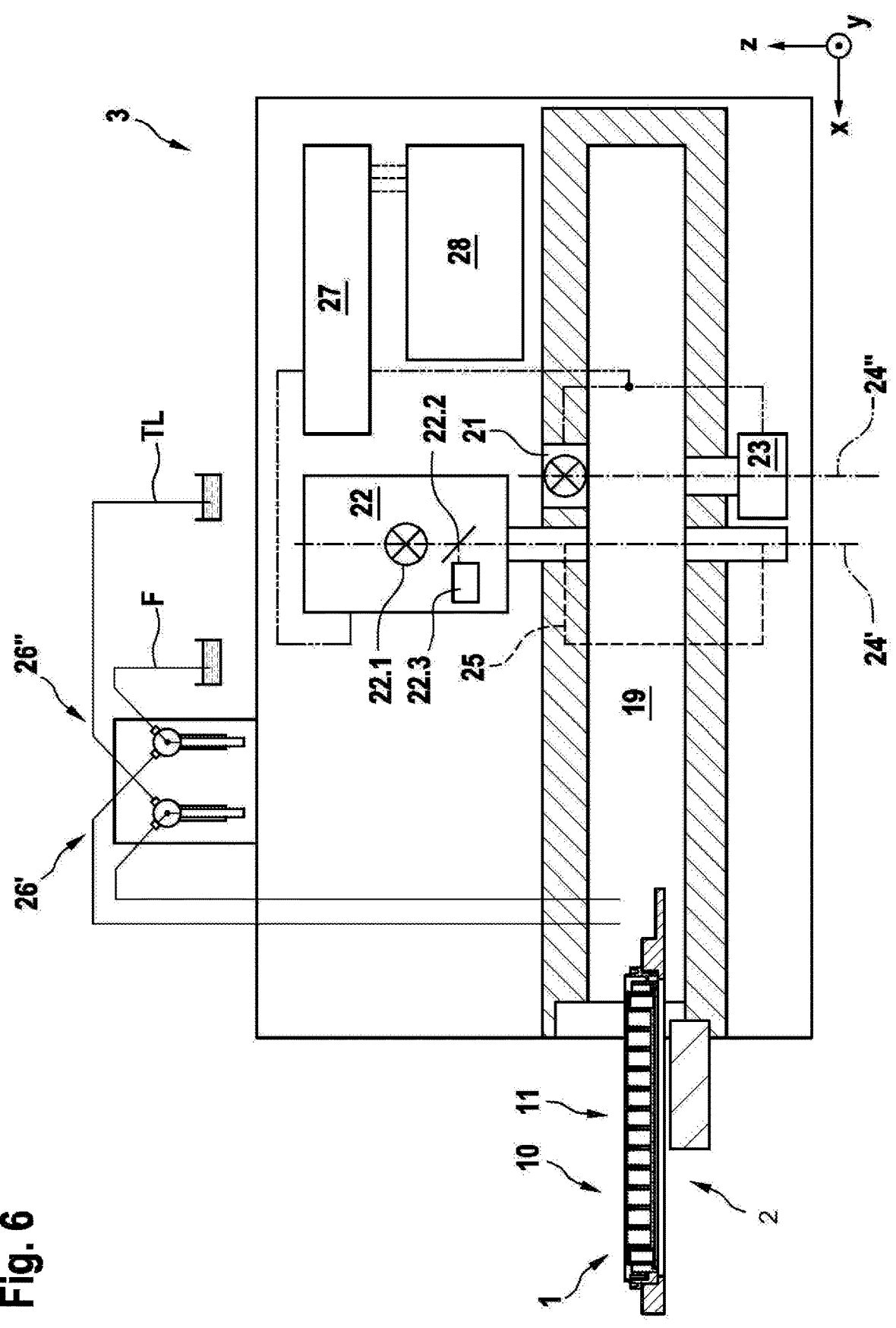
FIG. 6 shows a vertical section through a microplate reader, in which a transport support with an incubation cassette placed thereon and a microplate inserted therein is extended.

FIG. 6 shows a vertical section through a microplate reader 3 for drawing an incubation cassette 1 into a measuring chamber 19, wherein a microplate 10, e.g. a 96-well standard microplate, is inserted into the incubation cassette 1. Although not shown, the incubation cassette 1 may be covered with a lid. The microplate 10 includes, for example, wells containing biological structures. In the context of the present invention, the term "biological structures" includes: parts of tissue, e.g., of humans, animals or plants; cell cultures or parts thereof; single cells; cell organelles; Macromolecules such as nucleic acids or proteins as well as single molecules such as nucleotides, amino acids, hormones and metabolites.

The microplate reader 3 comprises the transport support 2 for receiving the incubation cassette 1. The transport support 2 can preferably be extended so far out of the measuring chamber 19 of the microplate reader 3 that the incubation cassette 1 can be placed by hand or by means of a microplate handling robot (not shown) on the transport support 2 or removed therefrom. The transport support 2 is shown here as already partially retracted because the microplate 10 and the incubation cassette 1 surrounding it are about to be pushed into the microplate reader 3. While the incubation cassette 1 is being pushed in or out, a flap is opened which, when closed, can close the measuring chamber 19, preferably in a light-tight and/or gas-tight manner, so that no light from the environment influencing the examinations can enter the measuring chamber 19 and/or so that the gas concentration in the measuring chamber 19 can be reliably controlled independently of the environment.

In addition to receiving the incubation cassette 1 equipped with the microplate 10, this transport support 2 also serves to position the microplate 10 with the wells containing biological structures (e.g. metabolites, macromolecules, cells or cell cultures) in relation to light sources 21, 22.1 and in relation to measuring devices 22.3, 23 of the microplate reader 3 or in relation to the optical axes 24', 24" of the measuring devices 22.3, 23. The light sources 21, 22.1 are used, for example, to bring about an interaction between at least one of these light sources 21, 22.1 and biological structures in certain wells of the microplate 10, and to cause or generate a measurable signal. Such signals include, for example, fluorescence emission, luminescence emission, reflected light and/or transmitted light.

In the fluorescence top-reading mode, a sample in a well is irradiated directly from above with the fluorescence module 22, and the emission light radiates back from the top of the sample. The emission light is guided to a first measuring device 22.3 via the semitransparent or dichroic mirror 22.2. In the bottom reading mode, the excitation light is guided under the microplate 10 via a light guide 25 and the sample is irradiated from below through the bottom of a respective well. The emission light reflects back down from the sample and is guided to the fluorescence module 22 via the light guide 25.

In the microplate reader shown, the second light source 21, including a device for wavelength selection, e.g. monochromator or wavelength filter, (not shown) serves to transmit radiation through a sample or biological structures in the wells of this microplate 10, and a second measuring device 23 (here e.g. in the form of a photodiode) for measuring the absorbance of the sample in relation to the second optical axis 24". The absorbance is hereby calculated by comparing the light intensity that has reached the second measuring device 23 through the sample with the transmitted reference light intensity. If, on the other hand, the luminescence of samples is to be detected, a light source can even be dispensed with and the light signal can be measured using e.g. photomultiplier tubes.

Such light sources are selected, for example, from a group comprising arc lamps, flash lamps, incandescent lamps (such as halogen lamps), lasers, laser diodes and light emitting diodes (LEDs). The appropriate wavelengths for exciting the fluorescence, as well as the corresponding fluorophores and their emission characteristics, are known to the person skilled in the art and are selected depending on the application. The person skilled in the art is also familiar with the non-invasive irradiation of cells or cell cultures to record the absorption, as well as the light sources to be used for this purpose. Measuring devices 22.3, 23 for detecting at least one integral signal caused or generated by the light source(s) 21, 22.1 in or on biological structures in the specific wells of the microplate 10 are preferably selected from a group comprising photomultipliers, photodiodes, photodiode arrays and avalanche diodes. The measuring devices 22.3, 23 and light sources 21, 22.1, or their optical input and/or output, are preferably coupled via light guides 25, such as optical fibers or optical fiber bundles.

A fluorescence module 22 of the microplate reader 3 can be used for monitoring or determining the liquid level in the liquid reservoir of the microplate 10 and/or incubation cassette 1 according to the invention. As described above, the liquid level of the liquid in the liquid reservoir of the incubation cassette 1 and/or microplate 10 is determined based on the determination of the height or the buoyancy of a float contained in a floating device. The height or the buoyancy of the float can be determined by measuring the fluorescence of the float.

In the exemplary embodiment shown, the fluorescence module 22 contains a first light source 22.1 including a device for wavelength selection, e.g. monochromator or wavelength filter (not shown) for illuminating the float (excitation light) along the first optical axis 24'. The fluorescence module 22 also contains a semi-transparent or dichroic mirror 22.2. The emission light is guided to the first measuring device 22.3 via this mirror 22.2. The mirror 22.2 serves to decouple the light reflected back from the float (emission light) from the path of the excitation light (=first optical axis 24').

In a fluorescence top-reading mode, the float is irradiated directly from above with the fluorescence module 22, and the emission light radiates back upwards from the float. In a fluorescence bottom-reading mode, the excitation light is guided via a light guide 25 under the incubation cassette 1 or microplate 10 and the float is irradiated from below through a transparent section of the incubation cassette 1 or e.g. through the transparent floor in the area of a liquid reservoir of the microplate 10. The emission light radiates downwards from the float and is guided to the fluorescence module 22 via the light guide 25.

The optics of the fluorescence module 22 can be focused on the uppermost position of the float, which this occupies when the liquid reservoir is completely filled. As the liquid level decreases, the float moves out of focus, causing the measured fluorescence (emitted by the float) of the float to decrease. The measured fluorescence thus correlates with the liquid level in the liquid reservoir. Based on the measured fluorescence, conclusions can be drawn about the liquid level in the liquid reservoir.

The optics of the fluorescence module 22 can be focused from below onto the lowermost position of the float, which this occupies when the liquid reservoir is empty. As the liquid level increases, the float moves out of focus, causing the measured fluorescence (emitted by the float) of the float to decrease. The measured fluorescence thus correlates with the liquid level in the liquid reservoir. Based on the measured fluorescence, conclusions can be drawn about the liquid level in the liquid reservoir. In the top reading mode, a maximum fluorescence signal is measured at the top position of the float (=full liquid reservoir). In the bottom reading mode, a maximum fluorescence signal is measured in the lowest position of the float (=empty liquid reservoir).

The incubation cassette 1 or microplate 10 can be moved relative to the first optical axis 24' of the microplate reader 3 in such a way that the first optical axis 24' strikes the float, either from directly above in the fluorescence top-reading mode or from below through one or more transparent sections of the incubation cassette 1 or microplate 10 in the fluorescence bottom-reading mode.

The liquid level of the liquid in the liquid channel of the incubation cassette 1 and/or the microplate 10 can thus be reliably measured by the fluorescence module 22. Further details on the fluorescence measurement preferably used here are described in connection with FIGS. 8A, B.

The microplate reader 3 further contains, for example, two injectors 26', 26", whereby a test solution TL is being dispensed into the wells of the microplate 10 via a first injector, also called test solution injector 26', and via a second injector, also called liquid injector 26", liquid F is filled or refilled into the liquid reservoir of the incubation cassette 1 and/or the microplate 10. The liquid reservoir is automatically filled, for example, as soon as the fluorescence module 22 of the microplate reader 3 detects by means of fluorescence measurement of the float that the level of the liquid in the liquid reservoir of the incubation cassette 1 and/or the microplate 10 has fallen below a predefined level. A controller 27, which is designed, for example, to control the first light source 22.1, the fluorescence module 22, the movement of the transport support 2 of the microplate reader 3, etc., can also be designed here to automate the dispensing of the liquid F into the liquid reservoir of the incubation cassette 1 and/or the microplate 10 by the second injector 26". It can thus be ensured that the liquid reservoir of the incubation cassette 1 and/or the microplate 10 is always sufficiently filled with liquid F, even in the case of e.g. long-lasting analyses.

The microplate reader 3 also includes an internal or integrated processor 28 or it is designed to be connectable to an external processor (not shown). Such a processor can thus be a microprocessor integrated into the electronic control of the microplate reader 3 or a personal computer provided.

Figure 7:
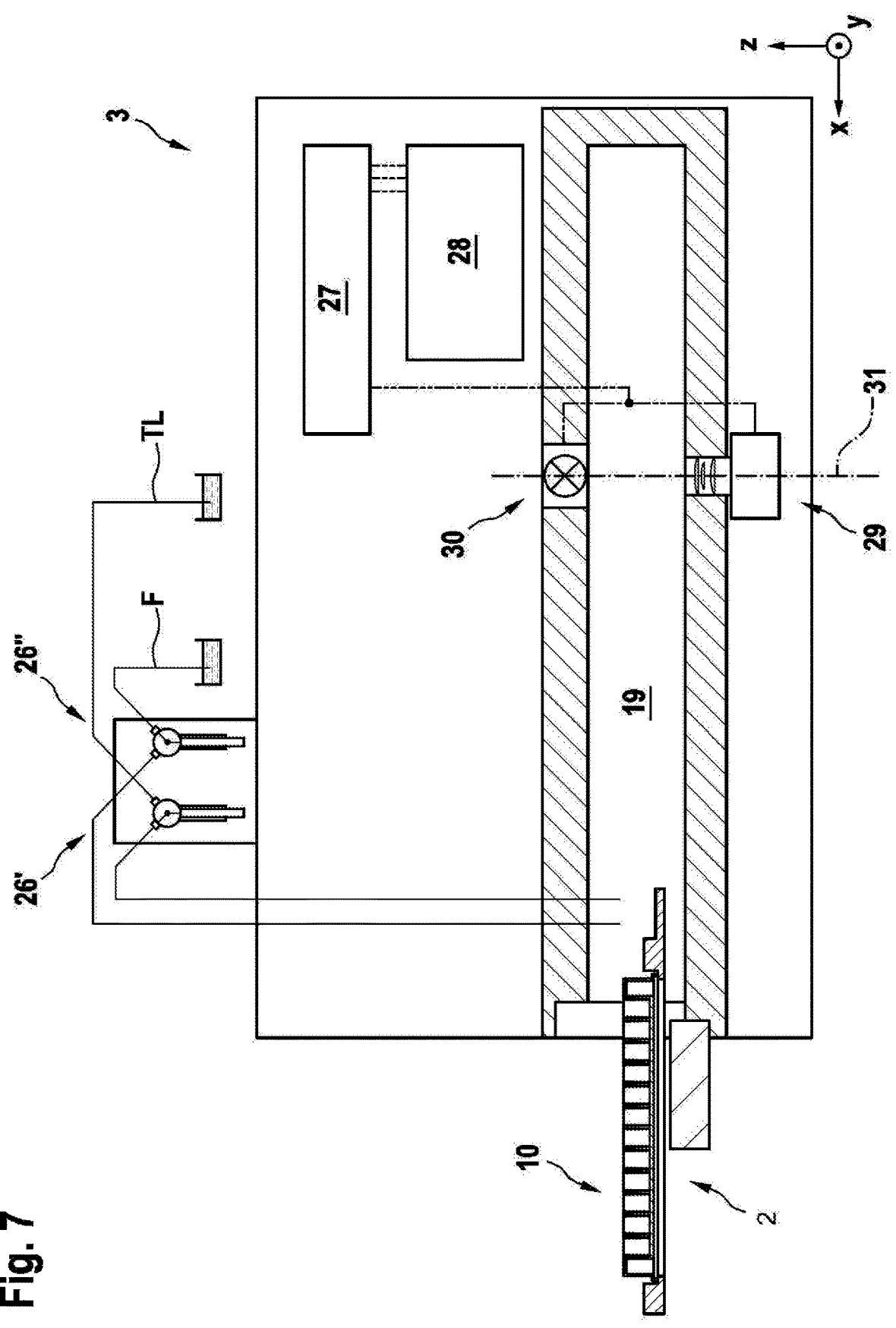
FIG. 7 shows a vertical section through a further microplate reader in which a transport support with a microplate placed on it is extended.

FIG. 7 shows a vertical section through a microplate reader 3 for drawing a microplate 10 (without an incubation cassette) into the measuring chamber 19. The microplate 10 can be completely transparent. In the embodiment shown, an arrangement made up of an imaging module with an optics/lens system 29 and an illumination source 30 is used. This illumination source 30 illuminates the microplate 10 from above. The imaging module with the optics/lens system 29 takes an image from below through the transparent bottom of a well of the microplate 10. The optics/lens system 29 can be designed to optically enlarge or reduce images. In addition to the illumination source 30 and the imaging module with the optics/lens system 29, the microplate reader 3 can have measurement modules as shown in FIG. 6.

FIGS. 8A, B show curves of a fluorescence measurement of the float in the top reading mode and a liquid level of a liquid taken up in the liquid reservoir derived therefrom, each plotted as a function of time.

For the fluorescence measurement, the float is excited with e.g. 240 nm (20 nm bandwidth) and measured at 320 nm (20 nm bandwidth). In an optimized way, the emission of the float used could also be measured at approx. 590 nm with the same excitation wavelength.

Figure 8B:
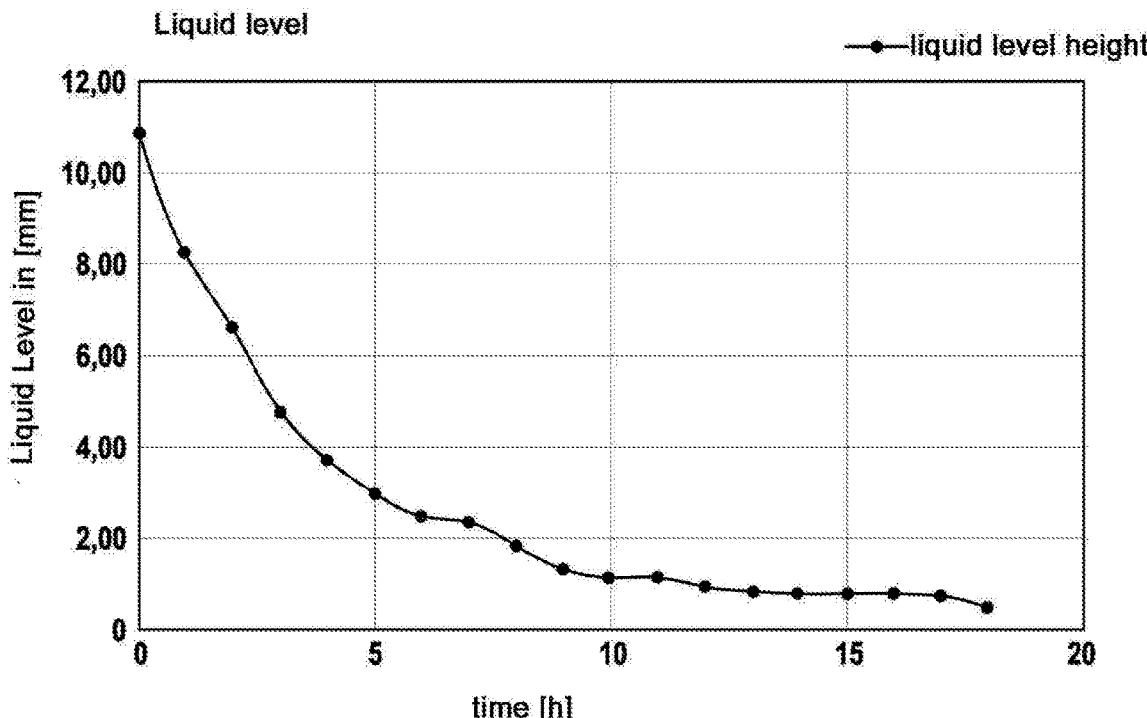

For fluorescence measurement, the optics of the fluorescence module can be focused on the uppermost position of the float, which this occupies when the liquid reservoir is completely filled (see FIG. 8A). A unit of relative fluorescence (Relative Fluorescence Units [RFU]) can be determined at a value of approx. 55000 RFU when the liquid reservoir is completely filled. As expected, the liquid level decreases with time due to evaporation. As the liquid level decreases, the float moves out of focus, causing the measured fluorescence (emitted by the float) of the float to decrease. The measured fluorescence correlates with the liquid level in the liquid reservoir (see FIG. 8B) and the measured fluorescence allows conclusions to be drawn about the liquid level in the liquid reservoir. In the example shown, a fall in the liquid level from initially approx. 11 mm to 0 cm is measured in approximately 18 hours. By precisely determining the liquid level, liquid can be refilled in the liquid reservoir in good time, e.g. if the liquid level is 6 mm, 4 mm, 2 mm, etc.

FIGS. 9A, B show a flow chart of a method for reducing liquid evaporation from wells of a microplate placed in an incubation cassette. FIGS. 10A, B show a flow chart of a method for reducing liquid evaporation from wells of a microplate.

With regard to the flowchart shown in FIGS. 9A, B, reference is made to the microplate readers shown in FIGS. 6 and 7, into which an incubation cassette is inserted, in which a microplate is inserted (FIG. 6) or only a microplate (without incubation cassette) is inserted into the microplate reader (FIG. 7).

Referring to the flowchart shown in FIGS. 9A, B, the method begins with a step S9_1 in which the transport support of the microplate reader is moved out. In a step S9_2, the incubation cassette is placed on the transport support. However, the incubation cassette can also be used permanently. In a step S9_3, the microplate is inserted into the incubation cassette. In a step S9_4, a lid is then placed on the incubation cassette. The transport support with the incubation cassette prepared in this way is moved into the microplate reader in a step S9_5. The lid is lifted off robotically in the microplate reader (step S9_6). The gas concentration is also measured in the microplate reader (e.g. the concentration of $O_2$, $CO_2$, etc.), and in a step S9_7 there is a wait until a predetermined gas concentration is reached. In addition, the temperature is measured in the microplate reader, and in a step S9_8 there is a wait until a predetermined target temperature is reached, e.g. 37° C. As soon as the predetermined gas concentration and/or target temperature are reached, in a step S9_9 the test solution is added by means of a test solution injector to predetermined wells of the microplate, e.g. those provided with substances. However, the test solution can also be added at an earlier point in time, e.g. outside the microplate reader, i.e. before the microplate is inserted into the microplate reader. Furthermore, in this step the liquid can be added to the liquid reservoir of the incubation cassette and/or the microplate. However, the liquid can also be added beforehand, e.g. outside the microplate reader, i.e. before the incubation cassette with the microplate is inserted into the microplate reader.

In a step S9_10, the samples in the wells are measured using measurement methods such as absorption, fluorescence, luminescence, imaging, etc. Subsequently, in a step S9_11, the lid is placed on the incubation cassette. This reduces the liquid evaporation from the wells of the microplate. In a step S9_12, a predetermined time interval is awaited, e.g. 1 hour, 2 hours, etc. After the predetermined time interval has elapsed, the lid is robotically lifted in a step S9_13. In a step S9_14, the samples in the respective wells are measured. Subsequently, in a step S9_15, the fill level of the liquid in the liquid reservoir of the incubation cassette and/or in the liquid reservoir of the microplate is measured, e.g. by measuring the fluorescence emitted by the float in top reading mode. In a step S9_16, based on the result of the filling level measurement, it is determined whether or not the filling level has fallen below a predetermined threshold value.

If it is determined in step S9_16 that the filling level has fallen below the threshold value (yes), the method continues with step S9_17, in which the liquid reservoir of the incubation cassette and/or the liquid reservoir of the microplate is transported by means of a transport support to an outlet of an injector tube for adding liquid. As soon as this position is reached, the corresponding liquid reservoir is filled or refilled or post-injected by the injector (step S9_18). The method then continues with a step S9_19 described later.

If it is determined in step S9_16 that the fill level has not fallen below the threshold value (no), the method continues with step S9_19, in which the lid is placed back robotically on the incubation cassette. In a subsequent step S9_20, it is determined whether a predetermined maximum number of measurement cycles has been exceeded. If it is determined in step S9_20 that the maximum number of measurement cycles has not been exceeded (no), the method returns to step S9_12. If it is determined in step S9_20 that the maximum number of measurement cycles has been exceeded (yes), the method continues with step S9_21, in which the transport support with the incubation cassette and the microplate inserted therein is moved out of the microplate reader. The process can then be terminated.

It should be noted that in the procedure the order of the steps can be changed. Likewise, the method described in the procedure is not to be considered restricted to the incubation cassette, the microplate inserted therein and the lid placed on the incubation cassette, as described above by way of example. In addition to the described incubation cassette with the lid in place, an incubation cassette without a lid can also be used, for example. In this case, for example, no robotics are required to lift the lid. In this case, no reservoir(s) may be present in the microplate. In this case, the measuring chamber of the microplate reader should be as small as possible. In addition to the automated refilling of the reservoir by the injector described here, refilling can also be done manually.

Referring to the flowchart shown in FIGS. 10A, B, reference is made to the microplate readers shown in FIGS. 6 and 7, into which an incubation cassette is inserted, in which a microplate is inserted (FIG. 6) or only one microplate (without incubation cassette) is inserted into the microplate reader (FIG. 7). The method starts with a step S10_1, in which the transport support of the microplate reader is moved out. In a step S10_2, the microplate is placed on the transport support. In a step S10_3, the transport support with the microplate placed on it is moved into the microplate reader. The gas concentration is measured in the microplate reader (e.g. the concentration of $O_2$, $CO_2$, etc.), and in a step S10_4 it is waited until a predetermined gas concentration is reached.

The temperature is also measured in the microplate reader, and in a step S10_5 there is a wait until a predetermined target temperature is reached. As soon as the predetermined gas concentration and/or target temperature has been reached, in step S10_6 the samples in the respective wells of the microplate are measured using measurement methods such as absorption, fluorescence, luminescence, imaging, etc., to generate a 'blank' value for the subsequent measurements. In a step S10_7, test solution is added to predetermined wells of the microplate, e.g. wells provided with substances, by means of a test solution injector. However, the test solution can also be added at an earlier point in time, e.g. outside the microplate reader, i.e. before the microplate is inserted into the microplate reader. Furthermore, in this step, the liquid can be added to the liquid reservoir of the microplate. However, the liquid can also be added beforehand, e.g. outside the microplate reader, i.e. before the microplate is inserted into the microplate reader. In a step S10_8, a predetermined period of time t can be awaited. In a step S10_9, the samples provided with the test solution can be measured in the respective wells. Subsequently, in a step S10_10, the fill level of the liquid in the liquid reservoir of the microplate is measured, for example, by measuring the fluorescence emitted by the float from below, for example using a top reading mode. In a step S10_11, based on the result of the aforementioned measurement, it is determined whether or not the filling level has fallen below a predetermined threshold value. For example, in the top reading mode, it can be determined whether or not the fluorescence signal falls below a threshold value as the float continues to sink. Alternatively, in a further example, it can be determined in the bottom reading mode whether or not a fluorescence signal threshold value has been exceeded as the float continues to sink.

If it is determined in step S10_11 that the filling level has fallen below the threshold value (yes), the method continues with step S10_12, in which an alarm can be output to a user of the microplate reader. In a step S10_13, the transport support is moved out of the microplate reader. As soon as the transport support has been moved out of the microplate reader, in a step S10_14 the liquid reservoir of the microplate is refilled with liquid, e.g. manually using a hand pipette. The transport support is then moved into the microplate reader (step S10_15). The method then continues with a step S10_16 described later.

If it is determined in step S10_11 that the filling level has not fallen below the threshold value (no), the method continues with step S10_16, in which it is determined whether a predetermined maximum number of measurement cycles has been exceeded.

If it is determined in step 10_16 that the maximum number of measurement cycles has not been exceeded (no), the method returns to step S10_8. If it is determined in step S10_16 that the maximum number of measurement cycles has been exceeded (yes), the method continues with step S10_17, in which the transport support with the microplate placed on it is moved out of the microplate reader. The process can then be ended.

It should be noted that the order of the steps in the procedure described can vary. Likewise, the method described in the procedure is not to be considered restricted to the microplate without a lid placed on it, as described above by way of example. In addition to the described microplate without an attached lid, a microplate with a lid can also be used, for example. The microplate is provided with at least one reservoir. If a microplate without a lid is used, no robotics are required in the microplate reader to lift off the lid. Here, too, the measuring chamber of the microplate reader should be as small as possible. The reservoir can be refilled by the injector or manually.

All processes described are to be regarded as examples and serve to explain the invention. Process steps described herein are not to be restricted to the sequences described. The respective sequences can be variable. Process steps may deviate from the sequence described.

The same reference symbols in the figures denote the same or at least similar features, even if these are not always described in detail.

| Reference numbers | |
|---|---|
| 1 | incubation cassette |
| 2 | transport support |
| 3 | microplate reader |
| 4 | frame, incubation frame |
| 5 | central first opening |
| 6 | inner wall |
| 7 | supporting surfaces of 4 |
| 8 | outer wall |
| 9 | liquid reservoir |
| 10 | microplate |
| 11 | lid |
| 12 | plate |
| 13 | magnetizable surface |
| 14 | intermediate floor |

-continued

| Reference numbers | |
| --- | --- |
| 17 | recess |
| 18 | ridge |
| 19 | measuring chamber |
| 21 | second light source |
| 22 | fluorescence module |
| 22.1 | first light source |
| 22.2 | semi-transparent or dichroic mirror |
| 22.3 | first measuring device |
| 23 | second measuring device |
| 24' | first optical axis |
| 24" | second optical axis |
| 25 | light guide |
| 26' | first injector |
| 26" | second injector |
| 27 | controller |
| 28 | processor |
| 29 | imaging module with optics-/lens system |
| 30 | illumination source |
| 31 | optical axis |
| 40 | floating device |
| 41 | guide section |
| 42 | stop |
| 43 | cap |
| 44 | grid |
| 45 | recess |
| F | liquid |
| TL | test solution |
| TA | transparent section |
| SK | float |

The invention claimed is:

1. A method for reducing liquid evaporation from wells of a microplate (10) comprising:

a) providing a microplate (10), b) adding a sample to at least one of the wells of the microplate (10), c) moving the microplate (10) or an incubation cassette (1) equipped with the microplate (10) into a microplate reader (3), d) injecting a liquid (F) into a liquid reservoir (9) provided in the microplate (10) and/or the incubation cassette (1), e) performing measurements on the sample in the respective well, f) measuring a liquid level in the liquid reservoir (9) of the microplate (10) and/or the incubation cassette (1) by measuring the buoyancy of a float (SK) provided in a floating device (40) in the liquid reservoir (9) of the microplate (10) and/or incubation cassette (1), the floating device (40) comprising a guide section (41) and said float (SK) is mounted to be guided by the guide section (41) and the float (SK) is mounted in an interior of the guide section (41) with the interior of the guide section (41) being able to be brought into fluid contact with the liquid (F) received in the liquid reservoir (9), in such a way that the float (SK) experiences buoyancy in relation to the liquid level of the liquid (F) received in the liquid reservoir (9), g) re-injecting the liquid (F) into the liquid reservoir (9) of the microplate (10) and/or the incubation cassette (1) when the liquid level falls below a predetermined threshold value, h) repeating steps e) to g) until a predetermined number of measurement cycles is reached, i) ejecting the microplate (10) or the incubation cassette (1) equipped with the microplate (10) from the microplate reader (3).

2. The method according to claim 1 wherein the incubation cassette (1) comprises a frame (4) for receiving a microplate (10) with wells, the frame (4) having a central first opening (5) surrounded by an inner wall (6) whose dimensions are designed for inserting a microplate (10), and the frame (4) comprises an outer wall (8) which extends parallel to the inner wall (6), which is connected via an intermediate floor (14) to the inner wall (6), so that by the two walls (6, 8) and the intermediate floor (14) the liquid reservoir (9) for receiving a liquid (F) and surrounding the first central opening (5) is formed, the incubation cassette (1) further comprising the float (SK) provided in the liquid reservoir (9), which can be brought into fluid contact with the liquid (F) held in the liquid reservoir (9), such that the float (SK) experiences buoyancy in relation to the liquid level of the liquid (F) received in the liquid reservoir (9).

3. The method according to claim 2, wherein the density of the float (SK) is lower than the density of the liquid (F) received.

4. The method according to claim 2, in which the guide section (41) is a hollow cylinder and the float (SK) is spherical.

5. The method according to claim 2, in which the guide section (41) is a hollow cylinder and the float (SK) is cylindrical.

6. The method according to claim 2, in which the float (SK) is triangular, square or star-shaped and the guide section (41) is designed correspondingly to the triangular, square or star-shaped design of the float (SK).

7. The method according to claim 2, in which the guide section (41) is designed in one piece with sections of the liquid reservoir (9).

8. The method according to claim 2, in which the guide section (41) can be removably connected to sections of the liquid reservoir (9).

9. The method according to claim 2, wherein the interior of the guide section (41) is exposed to the atmosphere.

10. The method according to claim 9, wherein the interior of the guide section (41) is exposed to the atmosphere via an opening provided at the upper end of the guide section (41).

11. The method according to claim 10, wherein the opening of the guide section (41) facing the atmosphere is provided with a stop (42) which is designed to retain the float (SK) in the guide section (41).

12. The method according to claim 2, wherein the intermediate floor (14) of the incubation cassette (1) is provided at least in sections with a transparent section (TA) in the region of the guide section (41).

13. The incubation cassette (1) according to claim 12, wherein the transparent section (TA) is optically transparent for light from an optical measuring device.

14. The method according to claim 2, wherein a section of the guide section (41) exposed to the liquid (F) in the liquid reservoir (9) is provided with at least one recess (45) via which the interior of the guide section (41) can be brought into fluid contact with the liquid (F) received in the liquid reservoir (9).

15. The method according to claim 1 wherein the microplate (10) comprises the liquid reservoir (9).

16. The method) according to claim 15, wherein the liquid reservoir (9) is provided between the wells and is delimited by a wall of the microplate (10) designed for receiving the liquid (F).

17. The method according to claim 15, wherein the density of the float (SK) is lower than the density of the liquid (F) received.

18. The method) according to claim 15, in which the guide section (41) is a hollow cylinder and the float (SK) is spherical.

19. The method according to claim 18, wherein the diameter of the float (SK) is equal to the inside diameter of the hollow cylinder.

20. The method according to claim 15, wherein the guide section (41) is a hollow cylinder and the float (SK) is cylindrical.

21. The method according to claim 15, the float (SK) being triangular, square or star-shaped and the guide section (41) being designed correspondingly to the triangular, square or star-shaped formation of the float (SK).

22. The method according to claim 15, wherein the guide section (41) is designed in one piece with sections of the liquid reservoir (9) of the microplate (10).

23. The method according to claim 15, in which the guide section (41) can be removably connected to sections of the liquid reservoir (9).

24. The method according to claim 15, wherein the interior of the guide section (41) is exposed to the atmosphere.

25. The method according to claim 24, wherein the interior of the guide section (41) is exposed to the atmosphere via an opening provided at the top.

26. The method according to claim 25, wherein the opening of the guide section (41) facing the atmosphere is provided with a stop (42) which is designed to hold back the float (SK) in the guide section (41).

27. The method according to claim 15, wherein the microplate (10) comprises at least one transparent section (TA) which is optically transparent to light from an optical measuring device.

28. The method according to claim 15, in which a section of the guide section (41) which is exposed to the liquid (F) in the liquid reservoir (9) is provided with at least one recess (45) via which the interior of the guide section (41) can be brought into fluid contact with the liquid (F) received in the liquid reservoir (9).

29. The method according to claim 15, wherein the microplate (10) further comprises ridges (18), which are provided between outer wells running parallel to an outside wall in each case, designed to subdivide the liquid reservoir (9) into at least two partial reservoirs.

30. The method according to claim 15, wherein the microplate is a standard microplate (10) according to the ANSI_SBS 1-2-3-4-2004 standard.

31. The method according to claim 1, further comprising injecting or post injecting the liquid (F) into the liquid reservoir (9) of the microplate (10) and/or the incubation cassette (1) by a liquid injector (26') included in the microplate reader (3) or manually.

32. The method according to claim 1, further comprising a step c1) of injecting a test solution (TL) into the sample in the well of the microplate (10) following step c).

33. The method according to claim 1, further comprising measuring the samples or the samples provided with the test solution by measuring absorbance, luminescence or fluorescence, or by imaging the samples.

34. The method according to claim 1, further comprising measuring a fluorescence of the float (SK) from above the microplate (10) and/or incubation cassette (1) through an opening in the guide section (41).

35. The method according to claim 1, further comprising measuring a fluorescence of the float (SK) from below the microplate (10) and/or incubation cassette (1) through a transparent section of the microplate (10) and/or incubation cassette (1).

\* \* \* \* \*